United States Patent
Marabout et al.

(10) Patent No.: US 6,221,879 B1
(45) Date of Patent: Apr. 24, 2001

(54) 8-AZABICYCLO[3.2.1] OCTANE-3-METHANAMINE DERIVATIVES AS LIGANDS OF D2 AND D3 DOPAMINE AND 5HT1A AND 5HT2 SEROTONIN RECEPTORS

(75) Inventors: Benoit Marabout, Chilly Mazarin; Mireille Sevrin, Paris; Pascal George, Saint Arnoult en Yvelines; Jean-Pierre Merly, Sceaux; Daniele De Peretti, Antony; Jocelyne Roy, Ris Orangis; David Machnik, Paris, all of (FR)

(73) Assignee: Sanofi-Synthelabo, Paris (FR)

( * ) Notice: Subject to any disclaimer, the term of this patent is extended or adjusted under 35 U.S.C. 154(b) by 0 days.

(21) Appl. No.: 09/529,077

(22) PCT Filed: Oct. 7, 1998

(86) PCT No.: PCT/FR98/02137

§ 371 Date: Jul. 14, 2000

§ 102(e) Date: Jul. 14, 2000

(87) PCT Pub. No.: WO99/19325

PCT Pub. Date: Apr. 22, 1999

(30) Foreign Application Priority Data

Oct. 9, 1997 (FR) .................................................. 97 12580
Oct. 9, 1997 (FR) .................................................. 97 12583

(51) Int. Cl.[7] .......................... A61K 31/46; C07D 451/02
(52) U.S. Cl. ......................... 514/304; 546/124; 546/126; 546/132; 546/112; 514/299
(58) Field of Search .................... 514/304, 299; 546/124, 112, 126, 132

(56) References Cited

U.S. PATENT DOCUMENTS

| | | |
|---|---|---|
| 4,273,778 | 6/1981 | Hadley et al. . |
| 4,544,660 | 10/1985 | Hadley et al. . |
| 4,910,302 | 3/1990 | Abou-Gharbia et al. . |
| 5,179,108 | 1/1993 | George et al. . |
| 5,286,735 | 2/1994 | Bonnaud et al. . |
| 5,318,988 | 6/1994 | Schohe-Loop et al. . |

FOREIGN PATENT DOCUMENTS

| | | |
|---|---|---|
| 81054 | 6/1983 | (EP) . |
| 447292 | 9/1991 | (EP) . |
| 532398 | 3/1993 | (EP) . |
| 540914 | 5/1993 | (EP) . |
| 2681325 | 3/1993 | (FR) . |
| WO 9420466 | 9/1994 | (WO) . |

OTHER PUBLICATIONS

Derwent Patent Abstract No. 199311.
Derwent Patent Abstract No. 199436.

*Primary Examiner*—C. S. Aulakh
(74) *Attorney, Agent, or Firm*—Michael D. Alexander

(57) ABSTRACT

Compounds of general formula (I)

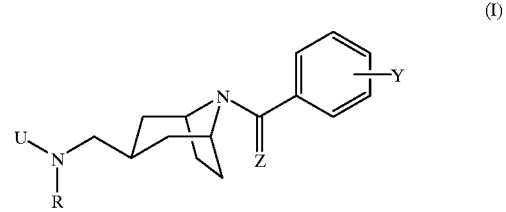

in which U represents a group of general formula (A) or (B)

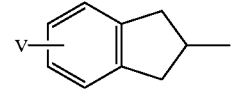

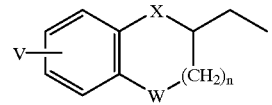

in which formulae V represents a hydrogen or halogen atom, a $(C_1-C_3)$alkyl group or one or two $(C_1-C_3)$alkoxy groups, W and X each represent, respectively, either two oxygen atoms, or an oxygen atom and a $CH_2$ group, or a $CH_2$ group and an oxygen atom, or an oxygen atom and a CO group, n represents the number 0 or 1, R represents either a propyl group when U represents a group of general formula (A), or a hydrogen atom or a $(C_1-C_3)$alkyl group when U represents a group of general formula (B), Y represents one or more atoms or groups chosen from the following: hydrogen, halogen, $(C_1-C_3)$alkyl and $(C_1-C_3)$alkoxy, Z represents two hydrogen atoms or an oxygen atom.

20 Claims, No Drawings

8-AZABICYCLO[3.2.1] OCTANE-3-METHANAMINE DERIVATIVES AS LIGANDS OF D2 AND D3 DOPAMINE AND 5HT1A AND 5HT2 SEROTONIN RECEPTORS

The present invention relates to compounds of general formula (I)

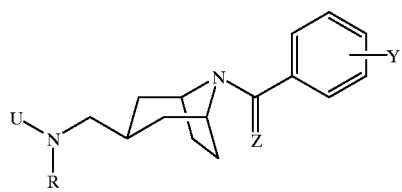

(I)

in which
U represents
A) either a 2,3-dihydro-1H-inden-2-yl group of general formula (A)

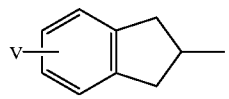

(A)

B) or a heterocyclic group of general formula (B) in which

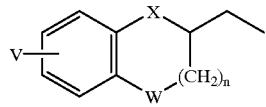

(B)

V represents a hydrogen or halogen atom, a $(C_1-C_3)$alkyl group or one or two $(C_1-C_3)$alkoxy groups, W and X each represent, respectively, either two oxygen atoms, or an oxygen atom and a $CH_2$ group, or a $CH_2$ group and an oxygen atom, or an oxygen atom and a CO group, n represents the number 0 or 1, R represents either a propyl group when U represents a 2,3-dihydro-1H-inden-2-yl group of general formula (A), or a hydrogen atom or a $(C_1-C_3)$alkyl group when U represents a heterocyclic group of general formula (B), Y represents one or more atoms or groups chosen from the following: hydrogen, halogen, $(C_1-C_3)$alkyl and $(C_1-C_3)$alkoxy, Z represents two hydrogen atoms or an oxygen atom.

The compounds of the invention can exist in two forms of geometrical isomers, namely the α, or endo, isomeric form in which the $CH_2$ group in the 3 position of the tropane ring-system (azabicyclooctane) is in an axial position, and the β, or exo, isomeric form in which the said $CH_2$ group is in an equatorial position, in the so-called "chair" conformation of the piperidine unit of the tropane ring-system.

The compounds of the invention can also exist in the form of bases or of addition salts with acids.

When U represents a 2,3-dihydro-1H-inden-2-yl group of general formula (A), the compounds of the invention correspond to the general formula (IA)

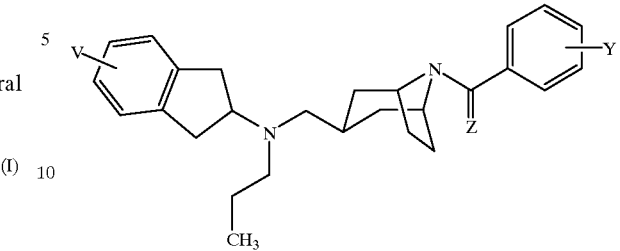

(IA)

They can be prepared according to a process illustrated by Scheme 1A which follows.

Scheme 1A

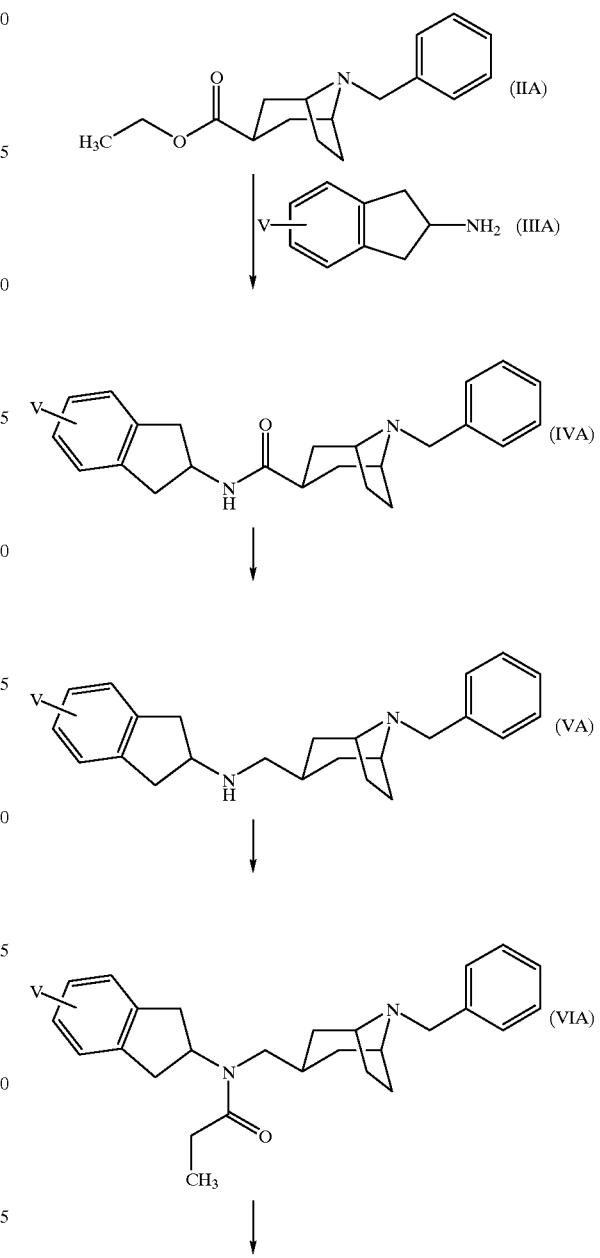

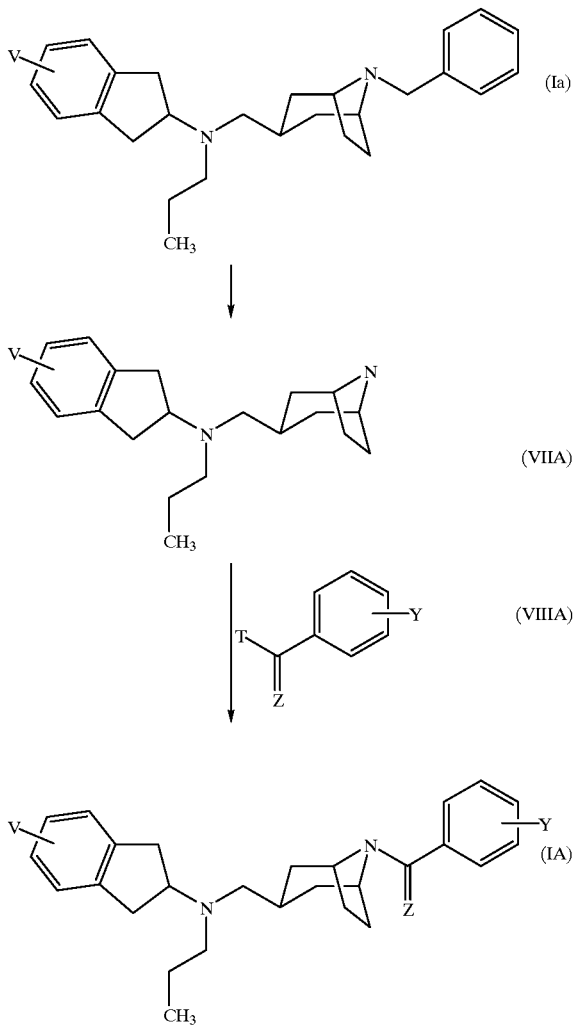

Ethyl 8-(phenylmethyl)-8-azabicyclo[3.2.1]-octane-3-carboxylate of formula (IIA) is reacted with a dimethylaluminium amide, prepared beforehand from trimethylaluminium and a 2,3-dihydro-1H-indene-2-amine derivative of general formula (IIIA), in which V is as defined above, in an inert solvent, for example toluene, at a temperature of from 0 to 100° C.; a compound of general formula (IVA) is obtained, which is reduced by the action of a mixed alkali metal hydride such as lithium aluminium hydride, in an ether solvent, for example tetrahydrofuran, at a temperature of from 0 to 60° C., to give a compound of general formula (VA). This compound is subjected to an acylation using propanoyl chloride, in a chlorinated solvent, for example dichloromethane, in the presence of a base such as triethylamine, at a temperature of from 0 to 40° C., to give an amide of general formula (VIA), which is reduced by the action of a mixed alkali metal hydride such as lithium aluminium hydride, in an ether solvent, for example tetrahydrofuran, at a temperature of from 0 to 60° C., to give a compound of general formula (Ia) which corresponds to the general formula (IA) when Y represents a hydrogen atom and Z represents two hydrogen atoms. To prepare another compound of general formula (IA), debenzylation is then carried out, for example by catalytic hydrogenation, to give the amine of general formula (VIIA), and finally this amine is reacted either with an acid chloride of general formula (VIIIA) in which Y is as defined above, Z represents an oxygen atom and T represents a chlorine atom, in a chlorinated solvent, for example dichloromethane, in the presence of a base such as triethylamine, at a temperature of from 20 to 40° C., or with a halogenated derivative of general formula (VIIIA) in which Y is as defined above, Z represents two hydrogen atoms and T represents a halogen atom, in an aprotic solvent, for example N,N-dimethylformamide, in the presence of a base such as potassium carbonate, at a temperature of from 20 to 100° C.

The 2,3-dihydro-1H-indene-2-amine of general formula (IIIA) in which X represents hydrogen is commercially available; the substituted derivatives of 2,3-dihydro-1H-indene-2-amine of general formula (IIIA) can be prepared by methods analogous to those described in *Can. J. Chem.* (1974) 52 381–389.

The ethyl 8-(phenylmethyl)-8-azabicyclo[3.2.1]octane-3-carboxylate of formula (IIA) can be prepared by a method analogous to that described in *J. Med. Chem.* (1994) 37 2831.

When U represents a heterocyclic group of general formula (B), the compounds of the invention correspond to the general formula (IB)

They can be prepared according to processes illustrated by Schemes 1B to 3B which follow.

Scheme IBa

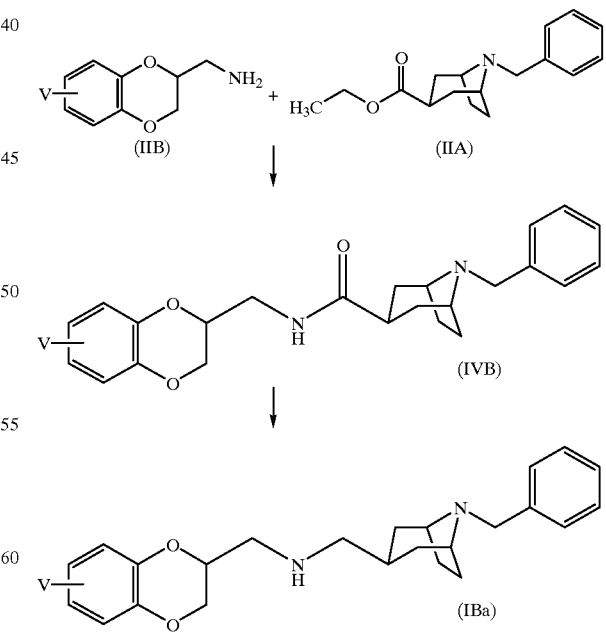

According to Schemes IBa, IBb and IBc, the compounds of general formula (IB), in which W and X each represent an oxygen atom and n represents the number 1, are prepared by reacting ethyl 8-(phenylmethyl)-8-azabicyclo[3.2.1]-octane-3-carboxylate of formula (IIA) with a dimethylaluminium amide, prepared beforehand from trimethylaluminium and a 2,3-dihydro-1,4-benzodioxane-2-methanamine derivative of general formula (IIB), in which V is as defined above, in an inert solvent such as toluene, at a temperature of from 0 to 100° C., to give a compound of general formula (IVB), which is reduced by the action of a mixed alkali metal hydride, for example lithium aluminium hydride, in an ether solvent such as tetrahydrofuran, at a temperature of from 0 to 60° C.

A compound of general formula (IBa) which corresponds to the general formula (IB) where R and Y each represent a hydrogen atom and Z represents two hydrogen atoms is obtained.

If a final compound is desired, in the general formula of which R represents a hydrogen atom or an alkyl group, the compound of general formula (IBa) is then treated by one of the processes illustrated by Schemes IBb or IBc.

Scheme IBb begins by protecting the secondary amine function of the compound of general formula (IBa) by the action of bis(1,1-dimethylethyl)dicarbonate; in a chlorinated solvent such as dichloromethane, to give a compound of general formula (VB), in which Boc represents a 1,1-dimethylethoxycarbonyl group. This compound is debenzylated by catalytic hydrogenation and the compound thus obtained, of general formula (VIB), is then reacted with an acid chloride of general formula (VIIB) in which Y is as defined above and Hal represents a chlorine atom, in a chlorinated solvent, for example dichloromethane, in the presence of a base such as triethylamine, at a temperature of from 20 to 40° C. A compound of general formula (VIIIB) is obtained, the secondary amine function of which is deprotected using trifluoroacetic acid to give a compound of general Scheme 1Bb

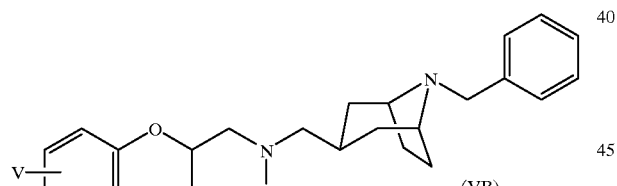

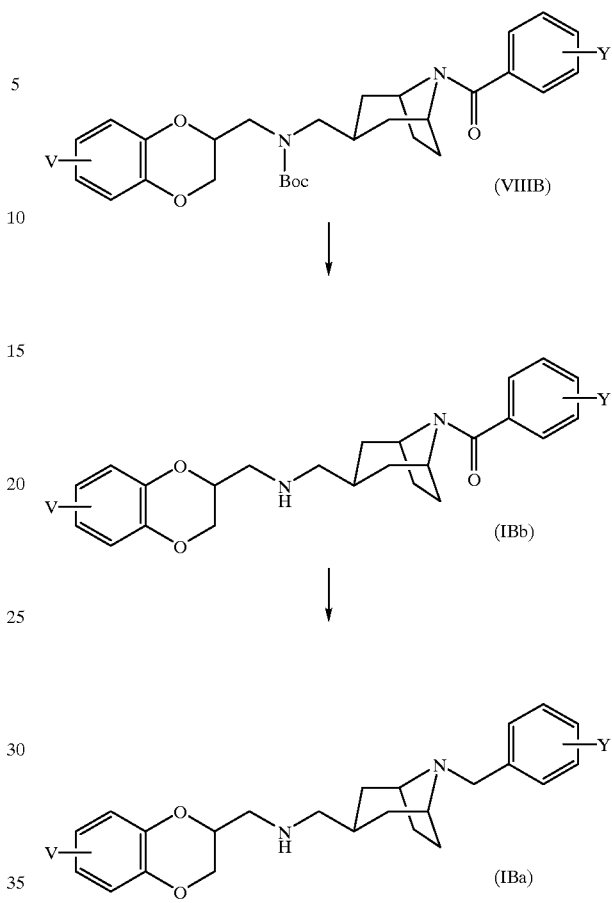

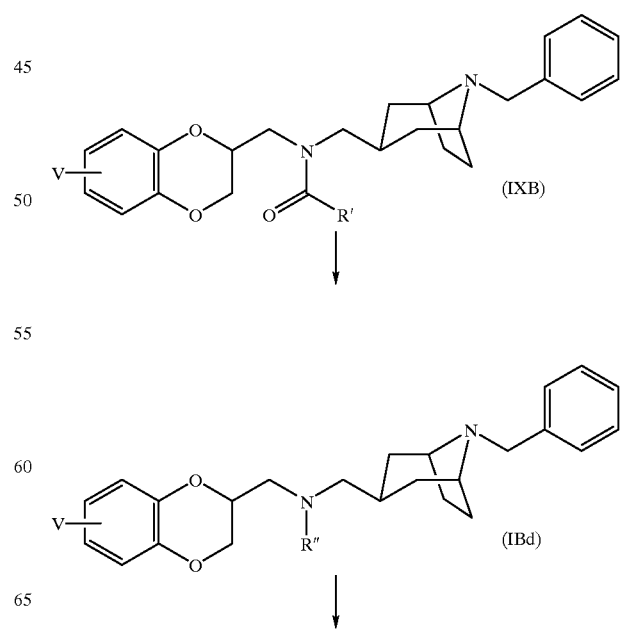

-continued

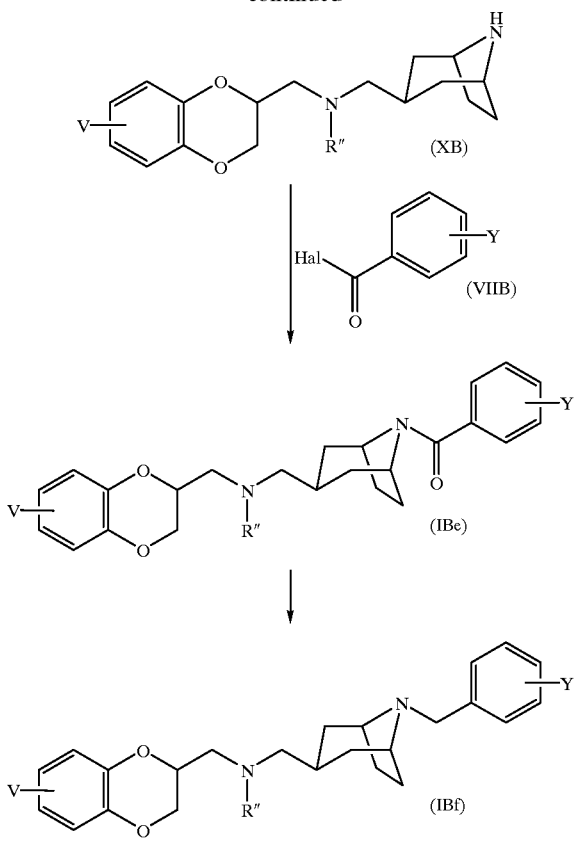

formula (IBb).

Finally, and if so desired, this compound is reduced by the action of a mixed alkali metal hydride, for example lithium aluminium hydride, in an ether solvent such as tetrahydrofuran, to give a compound of general formula (IBa).

In Scheme IBc, a compound of general formula (IBa) is subjected to an acylation using an acetic-forming mixed anhydride or a $C_2$–$C_3$ acid chloride, in a chlorinated solvent such as dichloromethane, at a temperature of from 0 to 40° C., to give a compound of general formula (IXB), in which R' represents a hydrogen atom or a methyl or ethyl group, and this acylated compound is then reduced using a mixed alkali metal hydride, for example lithium aluminium hydride, in an ether solvent such as tetrahydrofuran, to give a compound of general formula (IBd), in which R" represents a ($C_1$–$C_3$) alkyl group.

This compound is then treated as indicated with regard to the compound of general formula (VB), with the exception, of course, of the amine deprotect ion step.

In Scheme 2B, the compounds of general formula (IB), in which X represents an oxygen atom, W represents an oxygen atom or a $CH_2$, group, R represents a hydrogen atom and n represents the number 1, are prepared by reacting a compound of general formula (XIB), in which V is as defined above and G represents a leaving group such as a halogen atom or a methanesulphonyloxy or 4-methylbenzenesulphonyloxy group, with an 8-azabicyclo[3.2.1]octane-3-amine of general formula (XIIB), in which Y, Z and R are as defined above, in a solvent such as acetonitrile, in the presence of a base such as potassium carbonate.

In Scheme 3E, the compounds of general formula (IB), in which X represents a CO group, W represents an oxygen atom, R represents a hydrogen atom and n represents the number 1, are prepared by reacting a compound of general formula (XIIIB), in which V is as defined above, with paraformaldehyde and an 8-azabicyclo[3.2.1]octane-3-amine of general formula (XIIB), in which Y, Z and R are as defined above, in a solvent such as 2-propanol, in the presence of a catalytic amount of hydrochloric acid.

The starting compounds to be used in the processes illustrated by Schemes IB to 3B are commercially available or can be prepared according to methods identical or analogous to those described in the literature, in particular in patent applications EP-0,193,400 and EP-0,013,138 and in J. Med. Chem. (1983), 26 823, J. Med. Chem. (1989) 32 1402, and J. Med. Chem. (1994) 37 2831.

The examples which follow illustrate the preparation of a number of compounds of the invention. The elemental microanalyses and the IR and NMR spectra confirm the structures of the compounds obtained.

Scheme 2B

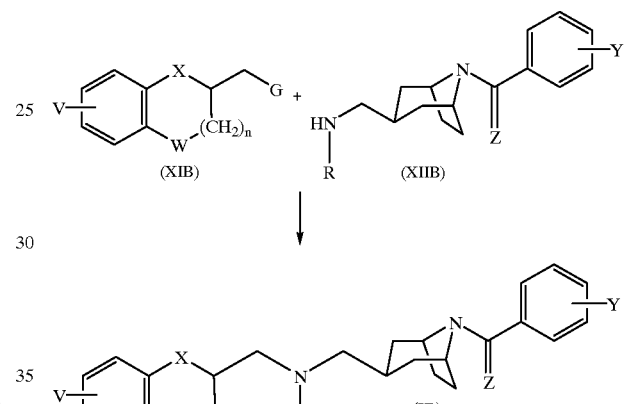

Scheme 3B

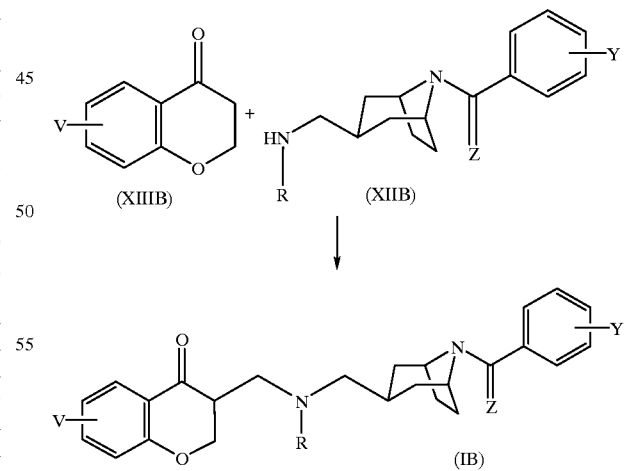

The numbers indicated in parentheses in the example titles correspond to those in the 1st column of Tables A and B given later.

In the compound names, the hyphen "—" forms part of the name, and the underscore line "_" serves merely to indicate the line break; it should be removed if a line break does not occur at that point and should not be replaced either with a normal hyphen or with a space.

EXAMPLE 1A (COMPOUND NO. 4A)

exo-N-(2,3-Dihydro-1H-inden-2-yl)-8-(phenylmethyl)-N-propyl-8-azabicyclo[3.2.1]octane-3-methanamine (E)-2-butenedioate (5:2)

1A.1. exo-N-(2,3-Dihydro-1H-inden-2-yl)-8-(phenylmethyl)-8-azabicyclo[3.2.1]octane-3-carboxamide.

20 ml of toluene are introduced into a 250 ml three-necked round-bottomed flask under an argon atmosphere, 1.48 g (20.4 mmol) of a 2 M solution of trimethylaluminium in heptane are added slowly, the mixture is cooled to 0° C. with a bath of ice, water and salt, 3.64 g (27.4 mmol) of 2,3-dihydro-1H-inden-2-amine are added dropwise, the mixture is heated at 50° C. for a few minutes, 3.6 g (13.2 mmol) of ethyl 8-(phenylmethyl)-8-azabicyclo[3.2.1]octane-3-carboxylate are then added at this temperature and the mixture is refluxed for 4 h.

It is cooled to 0° C. and hydrolysed by adding 24 ml of water, the resulting mixture is filtered through infusorial earth, the filtrate is dried over sodium sulphate and filtered and the solvents are evaporated off under reduced pressure.

The evaporation residue is purified by chromatography on a column of silica gel, eluting with a 97/3 to 93/7 mixture of dichloromethane and methanol.

4.56 g of solid are obtained.
Melting point: 129° C.

1A.2. exo-N-(2,3-Dihydro-1H-inden-2-yl)-8-(phenylmethyl)-8-azabicyclo[3.2.1]octane-3-methanamine (E)-2-butenedioate (2:1)

0.56 g (14.7 mmol) of lithium aluminium hydride suspended in 30 ml of tetrahydrofuran is introduced into a 250 ml three-necked round-bottomed flask under an argon atmosphere, the mixture is cooled to 0° C., 2.65 g (7.35 mmol) of exo-N-(2,3-dihydro-1H-inden-2-yl)-8-(phenylmethyl)-8-azabicyclo[3.2.1]octane-3-carboxamide dissolved in 50 ml of tetrahydrofuran are added and the mixture is refluxed for 12 h.

The mixture is cooled to 0° C., the excess hydride is hydrolysed with aqueous 1 N sodium hydroxide, the insoluble material is removed by filtration, the filtrate is dried over sodium sulphate and this solution is filtered and concentrated under reduced pressure.

2.55 g of oily product are obtained, the salt of which is prepared by addition of 1.7 g (14.7 mmol) of fumaric acid dissolved in 200 ml of ethanol to a solution of 2.55 g of the base in 50 ml of ethanol, the solvent is evaporated off under reduced pressure and the residue is recrystallized from a 4/1 mixture of methanol and ethanol.

2.9 g of fumarate are obtained.
Melting point: 216.5–219° C.

1A.3. exo-N-(2,3-Dihydro-1H-inden-2-yl)-N-[[8-(phenylmethyl)-8-azabicyclo[3.2.1]oct-3-yl-methyl]] propanamide hydrochloride 0.95 g (2.74 mmol) of exo-N-(2,3-dihydro-1H-inden-2-yl)-8-(phenylmethyl)-8-azabicyclo[3.2.1]octane-3-methanamine dissolved in 15 ml of dichloromethane is introduced into a 250 ml three-necked round-bottomed flask under an argon atmosphere, 0.31 g (3.02 mmol) of triethylamine is added, finally followed by dropwise addition of 0.27 g (2.88 mmol) of propanoyl chloride dissolved in 5 ml of dichloromethane, and the mixture is left stirring at room temperature for 5 h.

The mixture is washed with three times 50 ml of water, the organic phase is dried over sodium sulphate, filtered and concentrated under reduced pressure and the residue is purified by chromatography on a column of silica gel, eluting with a 98/2 to 92/8 mixture of dichloromethane and methanol.

0.9 g of base is obtained.

The hydrochloride is prepared by addition of 25 ml of a 0.1 N solution of hydrochloric acid in 2-propanol to a solution of 0.9 g (22.4 mmol) of base in 10 ml of ethyl acetate. The solvents are evaporated off under reduced pressure and the residue is recrystallized from a 9/1 mixture of ethyl acetate and 2-propanol.

0.65 g of white solid is obtained.
Melting point: 208–210° C.

1A.4. exo-N-(2,3-Dihydro-1H-inden-2-yl)-8-(phenylmethyl)-N-propyl-8-azabicyclo[3.2.1]octane-3-methanamine (E)-2-butenedioate (5:2).

0.34 g (8.94 mmol) of lithium aluminium hydride suspended in 20 ml of tetrahydrofuran is introduced into a 250 ml three-necked round-bottomed flask under an argon atmosphere, the mixture is cooled to 0° C., 1.8 g (4.47 mmol) of exo-N-(2,3-dihydro-1H-inden-2-yl)-N-[[8-(phenylmethyl)-8-azabicyclo[3.2.1]oct-3-yl]methyl] propanamide dissolved in 40 ml of tetrahydrofuran are added and the mixture is refluxed for 6 h.

The mixture is cooled to 0° C., the excess hydride is hydrolysed with aqueous 1 N sodium hydroxide, the insoluble material is removed by filtration, the filtrate is dried over sodium sulphate and the solution is filtered and concentrated under reduced pressure.

1.6 g of oily product are obtained.

The difumarate is prepared by addition of 0.96 g (8.24 mmol) of fumaric acid dissolved in 250 ml of ethanol to a solution of 1.6 g (4.12 mmol) of base in 100 ml of ethanol. The solvent is evaporated off under reduced pressure and the solid residue is recrystallized from a 95/5 mixture of ethanol and methanol.

After filtration and drying, 1.3 g of fumarate (5:2) are obtained.
Melting point: 190–192° C.

EXAMPLE 2A (COMPOUND NO. 5A)

exo-8-[(4-Chlorophenyl)methyl]-N-(2,3-dihydro-1H-inden-2-yl)-N-propyl-8-azabicyclo[3.2.1]octane-3-methanamine (E)-2-butenedioate (2:1)

2A.1. exo-N-(2,3-dihydro-1H-inden-2-yl)-N-propyl-8-azabicyclo[3.2.1]octane-3-methanamine.

A suspension of 1.75 g (4.5 mmol) of exo-N-(2,3-dihydro-1H-inden-2-yl)-8-(phenylmethyl)-N-propyl-8-azabicyclo[3.2.1]octane-3-methanamine in 40 ml of ethanol is prepared, 0.5 g of 10% palladium on charcoal is added and hydrogenation is carried out in Parr apparatus, at a pressure of about 0.32 MPa, at 45° C.

After cooling to room temperature, the catalyst is separated out by filtration, the filtrate is concentrated under reduced pressure, and the oily residue is taken up in aqueous ammonia solution and extracted with diethyl ether. The organic phase is washed with water, dried over sodium sulphate, filtered and concentrated under reduced pressure.

1.1 g of oily yellow residue are obtained, which product is used without further purification in the following step.

2A.2. exo-8-[(4-Chlorophenyl)methyl]-N-(2,3-dihydro-1H-inden-2-yl)-N-propyl-8-azabicyclo[3.2.1]octane-3-methanamine (E)-2-butenedioate (2:1)

2.94 g (9.8 mmol) of exo-N-(2,3-dihydro-1H-inden-2-yl)-N-propyl-8-azabicyclo[3.2.1]octane-3-methanamine dissolved in 45 ml of N,N-dimethylformamide, 2.2 g (10.7 mmol) of 1-bromomethyl-4-chlorobenzene, 2.7 g (19.6 mmol) of potassium carbonate and 0.1 g of sodium iodide are introduced into a 100 ml three-necked round-bottomed flask under an argon atmosphere and the mixture is then heated at 60° C. for 3 h. The mixture is allowed to cool and is poured onto 150 ml of ice-cold water and extracted with ethyl acetate. The organic phase is washed with water, dried over sodium sulphate and filtered, the filtrate is concentrated under reduced pressure and the residue is purified by chromatography on a column of silica gel, eluting with a 100/0 to 90/10 mixture of dichloromethane and methanol.

4.0 g of base are obtained, the fumarate of which is prepared by addition of 2.1 g (18.8 mmol) of fumaric acid dissolved in 50 ml of ethanol to 4.0 g (9.4 mmol) of base dissolved in 100 ml of ethanol, the solvent is evaporated off under reduced pressure and the residue is recrystallized from ethanol.

2.62 g of white solid are obtained.
Melting point: 198–199° C.

EXAMPLE 3A (COMPOUND NO. 3A)

exo-8-(3-Chlorobenzoyl)-N-(2,3-dihydro-1H-inden-2-yl)-N-propyl-8-azabicyclo[3.2.1]octane-3-methanamine hydrochloride 0.75 g (2.51 mmol) of exo-N-(2,3-dihydro-1H-inden-2-yl)-N-propyl-8-azabicyclo[3.2.1]octane-3-methanamine dissolved in 18 ml of dichloromethane is introduced into a 50 ml three-necked round-bottomed flask under an argon atmosphere, 0.51 g (5.03 mmol) of triethylamine is added, followed by slow addition of 0.88 g (5.02 mmol) of 3-chlorobenzoyl chloride, and the mixture is stirred at room temperature for 24 h. The mixture is poured onto 100 ml of water and extracted with ethyl acetate, the organic phase is separated out, washed with water, dried over sodium sulphate and filtered, the filtrate is concentrated under reduced pressure and the residue is purified by chromatography on a column of silica gel, eluting with a 99/1 to 98/2 mixture of dichloromethane and methanol.

0.2 g of base is obtained, the hydrochloride of which is prepared by addition of 5 ml of a 0.1 N solution of hydrochloric acid in 2-propanol to a solution of the 0.2 g (0.42 mmol) of base in 10 ml of ethyl acetate, the solvents are evaporated off under reduced pressure and the residue is recrystallized from a 95/5 mixture of ethyl acetate and 2-propanol.

0.12 g of white solid is obtained.
Melting point: 213–215° C.

EXAMPLE 4A (COMPOUND NO. 14A)

exo-N-(4,7-Dimethoxy-2,3-dihydro-1H-inden-2-yl)-8-(phenylmethyl)-N-propyl-8-azabicyclo[3.2.1]octane-3-methanamine (E)-2-butenedioate (2:1)

4A.1. exo-N-(4,7-dimethoxy-2,3-dihydro-1H-inden-2-yl)-8-(phenylmethyl)-8-azabicyclo[3.2.1]octane-3-carboxamide Using the procedure described in Example 1A.1, starting with 4.64 g (24 mmol) of 4,7-dimethoxy-2,3-dihydro-1H-indene-2-amine and 3.8 g (13.9 mmol) of ethyl 8-(phenylmethyl)-8-azabicyclo[3.2.1]octane-3-carboxylate, 4.1 g of solid are obtained, which product is used without further purification in the following step.

4A.2. exo-N-(4,7-Dimethoxy-2,3-dihydro-1H-inden-2-yl)-8-(phenylmethyl)-8-azabicyclo[3.2.1]octane-3-methanamine.

Using the procedure described in Example 1A.2, starting with 4.85 g (11.5 mmol) of exo-N-(4,7-dimethoxy-2,3-dihydro-1H-inden-2-yl)-8-(phenylmethyl)-8-azabicyclo[3.2.1]octane-3-carboxamide and 0.88 g (23 mmol) of lithium aluminium hydride, 4.6 g of oily product are obtained, which product is used without further purification in the following step.

4A.3. exo-N-(4,7-Dimethoxy-2,3-dihydro-1H-inden-2-yl)-N-[[8-(phenylmethyl)-8-azabicyclo[3.2.1]oct-3-yl]methyl]propanamide.

Using the procedure described in Example 1A.3, starting with 4.6 g (11.3 mmol) of exo-N-(4,7-dimethoxy-2,3-dihydro-1H-inden-2-yl)-8-(phenylmethyl)8-azabicyclo[3.2.1]octane-3-methanamine, 1.3 g (12.8 mmol) of triethylamine and 1.13 g (12.2 mmol) of propanoyl chloride, and after purification by chromatography on a column of silica gel, eluting with a 98/2 to 92/8 mixture of dichloromethane and methanol, 4.7 g of oily product are obtained, which product is used without further purification in the following step.

4A.4. exo-N-(4,7-Dimethoxy-2,3-dihydro-1H-inden-2-yl)-8-(phenylmethyl)-N-propyl-8-azabicyclo[3.2.1]octane-3-methanamine (E)-2-butenedioate (2:1).

Using the procedure described in Example 1A.4, starting with 4.7 g (10.1 mmol) of exo-N-(4,7-dimethoxy-2,3-dihydro-1H-inden-2-yl)-N-[[8-(phenylmethyl)-8-azabicyclo[3.2.1]oct-3-yl]methyl]propanamide and 0.78 g (20.6 mmol) of lithium aluminium hydride, and after purification by chromatography on a column of silica gel, eluting with a 96/4 to 88/12 mixture of dichloromethane and methanol, 4.5 g of compound are obtained in the form of a yellow oil.

1.0 g (2.23 mmol) of this product is dissolved in 100 ml of ethanol, a solution of 0.52 g (4.46 mmol) of fumaric acid in 100 ml of ethanol is added, the solvent is evaporated off under reduced pressure and the solid residue is recrystallized from ethanol.

0.68 g of fumarate (2:1) is obtained.
Melting point: 187–189° C.

EXAMPLE 5 (COMPOUND NO. 13A)

exo-N-(4,7-Dimethoxy-2,3-dihydro-1H-inden-2-yl)-8-(3-ethoxybenzoyl)-N-propyl-8-azabicyclo[3.2.1]octane-3-methanamine hydrochloride 5A.1. exo-N-(4,7-Dimethoxy-2,3-dihydro-1H-inden-2-yl)-N-propyl-8-azabicyclo[3.2.1]octane-3-methanamine.

Using the procedure described in Example 2A.1, starting with 4.95 g (11 mmol) of exo-N-(4,7-dimethoxy-2,3-dihydro-1H-inden-2-yl)-8-(phenylmethyl)-N-propyl-8-azabicyclo[3.2.1]octane-3-methanamine and 1.2 g of 10% palladium on charcoal, 3.4 g of oily compound are obtained, which product is used without further purification in the following step.

5A.2. exo-N-(4,7-Dimethoxy-2,3-dihydro-1H-inden-2-yl)-8-(3-ethoxybenzoyl)-N-propyl-8-azabicyclo[3.2.1]octane-3-methanamine hydrochloride.

Using the procedure described in Example 3A, starting with 1.1 g (3.07 mmol) of exo-N-(4,7-dimethoxy-2,3-dihydro-1H-inden-2-yl)-N-propyl-8-azabicyclo[3.2.1]octane-3-methanamine, 0.62 g (6.14 mmol) of triethylamine and 1.13 g (6.12 mmol) of 3-ethoxybenzoyl chloride, and after purification by chromatography on a column of silica gel, eluting with a 99/1 to 96/4 mixture of dichloromethane and methanol, 1.43 g of compound are obtained in the form of an oil.

The hydrochloride is prepared by addition of 30 ml of a 0.1N solution of hydrochloric acid in 2-propanol to a solution of 1.43 g (2.82 mmol) of base in 30 ml of ethanol, the solvents are evaporated off under reduced pressure and the solid residue is recrystallized from a 9/1 mixture of ethyl acetate and ethanol.

0.56 g of white solid is obtained.
Melting point: 161–163° C.

EXAMPLE 6A (COMPOUND NO. 12A)

exo-8-(3,4-Dimethoxybenzoyl)-N-(4,7-dimethoxy-2, 3-dihydro-1H-inden-2-yl)-N-propyl-8-azabicyclo [3.2.1]octane-3-methanamine hydrochloride Using the procedure described in Example 3A, starting with 1.25 g (3.49 mmol) of exo-N-(4,7-dimethoxy-2,3-dihydro-1H-inden-2-yl)-N-propyl-8-azabicyclo[3.2.1] octane-3-methanamine, 0.71 g (6.98 mmol) of triethylamine and 1.4 g (6.96 mmol) of 3,4-dimethoxybenzoyl chloride, and after purification by chromatography on a column of silica gel, eluting with a 99/1 to 96.5/3.5 mixture of dichloromethane and methanol, 1.5 g of compound are obtained in the form of a yellow oil.

The hydrochloride is prepared by addition of 30 ml of a 0.1N solution of hydrochloric acid in 2 -propanol to a solution of 1.5 g (2.87 mmol) of base in 30 ml of ethanol, the solvents are evaporated off under reduced pressure and the solid residue is recrystallized from a 9/1 mixture of ethyl acetate and ethanol.

1.12 g of white solid are obtained.
Melting point: 134–136° C.

EXAMPLE 1B (COMPOUND NO. 1B)

exo-N-[(2,3-Dihydro-1,4-benzodioxan-2-yl)methyl]-8-(phenylmethyl)-8-azabicyclo[3.2.1]octane-3-methanamine (E)-2-butenedioate (2:1)

1B.1. exo-N-[(2,3-dihydro-1,4-benzodioxan-2-yl)methyl]-8-(phenylmethyl)-8-azabicyclo[3.2.1]octane-3-carboxamide.

20 ml of a 2M solution of trimethylaluminium in toluene are introduced into a 500 ml three-necked round-bottomed flask under a nitrogen atmosphere, the mixture is cooled to 0° C., 7.75 g (39.7 mmol) of 2,3-dihydro-1,4-dioxane-2-methanamine dissolved in 150 ml of toluene are added dropwise, the mixture is heated to 50° C., 6.9 g (25.1 mmol) of ethyl 8-(phenylmethyl)-8-azabicyclo[3.2.1]octane-3-carboxylate dissolved in 35 ml of toluene are then added at this temperature and the mixture is refluxed for 8 h.

The mixture is cooled to 0° C. and hydrolysed by adding 50 ml of water, it is filtered over infusorial earth, the filtrate is dried over sodium sulphate, the solution is filtered and the solvents are evaporated off under reduced pressure.

The residue is purified by chromatography on a column of silica gel, eluting with 95/5 mixture of dichloromethane and methanol.

8.4 g of compound are obtained in the form of an oil.
1B.2. exo-N-[(2,3-Dihydro-1,4-benzodioxan-2-yl)methyl]-8-(phenylmethyl)-8-azabicyclo[3.2.1]octane-3-methanamine (E)-2-butenedioate (2:1).

5 g (131 mmol) of lithium aluminium hydride suspended in 50 ml of tetrahydrofuran are introduced into a 1 l three-necked round-bottomed flask under a nitrogen atmosphere, the mixture is cooled to 0°C., 8.4 g (21.4 mmol) of exo-N-[(2,3-dihydro-1,4-benzodioxan-2-yl)methyl]-8-(phenylmethyl)-8-azabicyclo[3.2.1]octane-3-carboxamide dissolved in 420 ml of tetrahydrofuran are added and the mixture is refluxed for 15 h.

The mixture is cooled to 0° C., the excess hydride is hydrolysed with aqueous 1 N sodium hydroxide, the insoluble material is removed by filtration and the filtrate is dried over sodium sulphate and concentrated under reduced pressure.

7.3 g of base are obtained in oily form.

2.9 g (7.66 mmol) of this product are taken, 1.8 g (15.5 mmol) of fumaric acid dissolved in ethanol are added, the solvent is evaporated off and the residue is recrystallized from 2-propanol and then from ethanol.

1.3 g of white solid are obtained.
Melting point: 105–107° C.

EXAMPLE 2B (COMPOUND NO. 15B)

exo-N-[(2,3-Dihydro-1,4-benzodioxan-2-yl)methyl]-8-(4-methoxybenzoyl)-8-azabicyclo[3.2.1]octane-3-methanamine hydrochloride (1:1)

2B.1. 1,1-Dimethylethyl exo-[(2,3-dihydro-1,4-benzodioxan-2-yl)methyl][[8-(phenylmethyl)-8-azabicyclo[3.2.1]oct-3-yl]methyl]carbamate.

7.3 g (193 mmol) of exo-N-[(2,3-dihydro-1,4-benzodioxan-2-yl)methyl]-8-(phenylmethyl)-8-azabicyclo [3.2.1]octane-3-methanamine dissolved in 18 ml of dichloromethane are introduced into a three-necked round-bottomed flask under a nitrogen atmosphere, 4.6 g (21 mmol) of bis(1,1-dimethylethyl) dicarbonate dissolved in 18 ml of dichloromethane are added dropwise and the mixture is stirred at room temperature for 24 h.

The solvent is evaporated off under reduced pressure, the residue is dissolved in 100 ml of diethyl ether, the solution is washed with water, dried over sodium sulphate and filtered, and the filtrate is concentrated under reduced pressure.

8.8 g of crude product are obtained, which product is purified by chromatography on a column of silica gel, eluting with a 92.5/7.5 mixture of dichloromethane and methanol.

7.7 g of compound are obtained in the form of an oil.
2B.2. 1,1-Dimethylethyl exo-[(2,3-dihydro-1,4-benzodioxan-2-yl)methyl](8-azabicyclo-[3.2.1]oct-3-ylmethyl)carbamate.

A solution of 7.4 g (15.45 mmol) of 1,1-dimethylethyl exo-[(2,3-dihydro-1,4-benzodioxan-2-yl)methyl][[8-(phenylmethyl)-8-azabicyclo[3.2.1]oct-3-yl]methyl] carbamate in 240 ml of ethanol is prepared, 3.5 g of 10 palladium on charcoal are added and a hydrogenation is carried out in Parr apparatus at 35° C. at a pressure of 0.30 MPa.

After cooling to room temperature, the catalyst is separated out by filtration and the filtrate is concentrated under reduced pressure.

5.23 g of oily residue are obtained, which product is used without further purification in the following step.
2B.3. 1,1-Dimethylethyl exo-[(2,3-dihydro-1,4-benzodioxan-2-yl)methyl][[8-(4-methoxybenzoyl)-8-azabicyclo[3.2.1]oct-3-yl]methyl]carbamate.

2 g (5.15 mmol) of 1,1-dimethylethyl exo-[(23-dihydro-1,4-benzodioxan-2-yl)methyl](8-azabicyclo[3.2.1]oct-3-ylmethyl)carbamate, 52 ml of N,N-dimethylformamide and 0.71 g (5.15 mmol) of potassium carbonate are introduced into a 250 ml three-necked round-bottomed flask under a nitrogen atmosphere, the mixture is heated to 50° C., 1 g (5.66 mmol) of 4-methoxybenzoyl chloride is added and the mixture is stirred at 50° C. for 10 h.

The solvent is evaporated off under reduced pressure, 50 ml of water and 300 ml of ethyl acetate are added to the residue, the organic phase is separated out, washed with water, dried over sodium sulphate and filtered, the filtrate is concentrated under reduced pressure and the residue is purified by chromatography on a column of silica gel, eluting with a 92/8 mixture of dichloromethane and methanol.

2.5 g of compound are obtained, which product is used without further purification in the following step.

2B.4. exo-N-[(2,3-Dihydro-1,4-benzodioxan-2-yl)methyl]-8-(4-methoxybenzoyl)-8-azabicyclo[3.2.1]octane-3-methanamine hydrochloride (1:1)

2.5 g (48 mmol) of 1,1-dimethylethyl exo-[(2,3-dihydro-1,4-benzodioxan-2-yl)methyl][[8-(4-methoxybenzoyl)-8-azabicyclo[3.2.1]oct-3-yl]methyl]carbamate, 25 ml of dichloromethane and 25 ml of trifluoroacetic acid are introduced into a 100 ml round-bottomed flask and the mixture is refluxed for 6 h.

The mixture is cooled, 30 ml of aqueous 10 N sodium hydroxide solution are added dropwise, the aqueous phase is separated out and extracted with dichloromethane, the organic phase is washed with water, dried over sodium sulphate and filtered, the filtrate is concentrated under reduced pressure and the residue is purified by chromatography on a column of silica gel, eluting with a 96/4 mixture of dichloromethane and methanol.

0.85 g of base is obtained, which is converted into the hydrochloride by addition of diethyl ether saturated with gaseous hydrogen chloride.

0.45 g of white solid is obtained,
Melting point: 93–110° C.

EXAMPLE 3B (COMPOUND NO. 12B)

exo-N-[(2,3-Dihydro-1,4-benzodioxan-2-yl)methyl]-8-(3-fluorobenzoyl)-8-azabicyclo[3.2.1]octane-3-methanamine hydrochloride (1:1)

3B1. 1,1-Dimethylethyl exo-[(2,3-dihydro-1,4-benzodioxan-2-yl)methyl][[8-(3-fluorobenzoyl)-8-azabicyclo[3.2.1]oct-3-yl]methyl]carbamate.

Using the procedure described in Example 2B.3, starting with 3.5 g (9 mmol) of 1,1-dimethylethyl exo-[(2,3-dihydro-1,4-benzodioxan-2-yl)methyl](8-azabicyclo[3.2.1]oct-3-ylmethyl)carbamate and 1.57 g (99 mmol) of 3-fluorobenzoyl chloride, in the presence of a catalytic amount of, potassium iodide, 2.7 g of oily product are obtained, which product is used without further purification in the following step.

3B.2. exo-N-[(2,3-Dihydro-1,4-benzodioxan-2-yl)methyl]-8-(3-fluorobenzoyl)-8-azabicyclo[3.2.1]octane-3-methanamine hydrochloride (1:1)

Using the procedure described in Example 2B.4, starting with 2.7 g (5.28 mmol) of 1,1-dimethylethyl exo-[(2,3-dihydro-1,4-benzodioxan-2-yl)methyl][[8-(3-fluorobenzoyl)-8-azabicyclo[3.2.1]oct-3-yl]methyl]carbamate, and after purification by chromatography on a column of silica gel, eluting with a 96.5/3.5 mixture of dichloromethane and methanol, 1.6 g of compound are obtained in the form of base.

The hydrochloride is prepared by treating 0.5 g of base with a 0.1 N solution of hydrochloric acid in 2-propanol, the solvent is evaporated off and the residue is recrystallized from ethyl acetate.

0.4 g of white solid is finally isolated.
Melting point: 206–209° C.

EXAMPLE 4B (COMPOUND NO. 4B)

exo-N-[(2,3-Dihydro-1,4-benzodioxan-2-yl)methyl-8-(3-fluorophenyl)-8-azabicyclo[3.2.1]octane-3-methanamine (E)-2-butenedioate (1:1).

0.25 g (6.6 mmol) of lithium aluminium hydride, 10 ml of tetrahydrofuran and 1 g (2.4 mmol) of exo-N-[(2,3-dihydro-1,4-benzodioxan-2-yl)methyl]-8-(3-fluorobenzoyl)-8-azabicyclo[3.2.1]octane-3-methanamine dissolved in 60 ml of tetrahydrofuran are introduced into a 250 ml three-necked round-bottomed flask under a nitrogen atmosphere and the mixture is stirred at the reflux temperature for 2 h and then at room temperature for 24 h.

The mixture is cooled to 0° C., the excess hydride in hydrolysed with aqueous 1 N sodium hydroxide, the insoluble material is removed by filtration, the filtrate is dried over sodium sulphate, this solution is filtered, the filtrate is concentrated under reduced pressure and the residue is purified by chromatography on a column of silica gel, eluting with a 93/7 mixture of dichloromethane and methanol.

0.6 g of base is obtained, which is dissolved in 5 ml of ethanol, 0.35 g (3 mmol) of fumaric acid is added and the product is left to crystallize by cooling.

0.2 g of furnarate is obtained.
Melting point: 132–134° C.

EXAMPLE 5B (COMPOUND NO. 8B)

exo-N-[(2,3-Dihydro-1,4-benzodioxan-2-yl)methyl]-8-(phenylmethyl)-N-propyl-8-azabicyclo[3.2.1] octane-3-methanamine (E)-2-butenedicate (2:1).

5B.1. exo-N-[(2,3-Dihydro-1,4-benzodioxan-2-yl)methyl]-N-[[-(phenylmethyl)-8-azabicyclo[3.2.1]oct-3-yl]methyl] propanamide.

3 g (7.9 mmol) of exo-N-[(2,3-dihydro-1,4-benzodioxan-2-yl)methyl]-8-(phenylmethyl)-8-azabicyclo[3.2.1]octane-3-methanamine, 100 ml of dichloromethane and 0.75 g (8.7 mmol) of propanoyl chloride dissolved in 10 ml of dichloromethane are introduced into a 250 ml three-necked round-bottomed flask and the mixture is stirred at room temperature for 20 h.

The mixture is washed with three times 50 ml of water, the organic phase is dried over sodium sulphate and filtered, the filtrate is concentrated under reduced pressure and the residue is purified by chromatography on silica gel, eluting with a 94/6 mixture of dichloromethane and methanol. 1.6 g of compound are obtained, which product is used without further purification in the following step.

5B.2. exo-N-[(2,3-Dihydro-1,4-benzodioxan-2-yl)methyl]-8-(phenylmethyl)-N-propyl-8-azabicyclo[3.2.1]octane-3-methanamine (E)-2-butenedioate (2:1)

0.3 g (7.4 mmol) of lithium aluminium hydride and 15 ml of tetrahydrofuran are introduced into a 100 ml three-necked round-bottomed flask under a nitrogen atmosphere, the mixture is cooled to 0° C., 1.6 g (3.7 mmol) of exo-N-[(2, 3-dihydro-1,4-benzodioxan-2-yl)methyl]-N-[[8-(phenylmethyl)-8-azabicyclo[3.2.1]oct-3-yl]methyl] propanamide dissolved in 32 ml of tetrahydrofuran are added and the mixture is refluxed for 7 h.

The mixture is cooled to 0° C., the excess hydride is hydrolysed with aqueous 1 N sodium hydroxide, the insoluble material is removed by filtration, the filtrate is dried over sodium sulphate, this solution is filtered and the filtrate is concentrated under reduced pressure. The fumarate is prepared from 1.45 g (3.44 mmol) of base dissolved in 5 ml of ethanol and 0.8 g (6.9 mmol) of fumaric acid dissolved in 10 ml of ethanol. The precipitate is collected by filtration and is recrystallized from ethanol.

1.1 g of white solid are obtained.
Melting point: 190–191° C.

EXAMPLE 6B (COMPOUND NO. 21B)

exo-N-[(2,3-Dihydro-1,4-benzodioxan-2-yl)methyl]-
8-(4-methylbenzoyl)-N-propyl-8-azabicyclo[3.2.1]
octane-3-methanamine hydrochloride (1:1)

6B.1. exo-N-[(2,3-Dihydro-1,4-benzodioxan-2-yl)methyl]-
N-propyl-8-azabicyclo[3.2.1]octane-3-methanamine 3.45 g (8.2 mmol) of exo-N-[(2,3-dihydro-1,4-benzodioxan-2-yl)methyl]-8-(phenylmethyl)-N-propyl-8-azabicyclo[3.2.1]octane-3-methanamine, 70 ml of methanol, 3.4 g of 10% palladium on charcoal and 3.4 g of ammonium formate are introduced into a 250 ml round-bottomed flask under a nitrogen atmosphere and the mixture is refluxed for 2 h. The mixture is left to cool, the catalyst is removed by filtration, the solvent is evaporated off under reduced pressure, the residue is dissolved in dichloromethane, the solution is washed with water, dried over sodium sulphate and filtered and the filtrate is concentrated under reduced pressure. 1.8 g of compound are obtained, which product is used without further purification in the following step.

6B.2. exo-N-[(2,3-Dihydro-1,4-benzodioxan-2-yl)methyl]-
8-(4-methylbenzoyl)-N-propyl-8-azabicyclo[3.2.1]
octane-3-methanamine hydrochloride (1:1)

1 g (3 mmol) of exo-N-[2,3-dihydro-1,4-benzodioxan-2-yl)methyl]-N-propyl-8-azabicyclo[3.2.1]octane-3-methanamine, 10 ml of tetrahydrofuran, 10 ml of ethyl acetate and 0.31 g (3 mmol) of triethylamine are introduced into a 100 ml three-necked round-bottomed flask under a nitrogen atmosphere. The mixture is cooled to 0° C., 0.51 g (3.3 mmol) of 4-methylbenzoyl chloride dissolved in 1 ml of ethyl acetate is added dropwise and the mixture is stirred at room temperature for 5 h.

The triethylamine hydrochloride is removed by filtration, the filtrate is concentrated under reduced pressure, the residue is dissolved in dichloromethane, the solution is washed with water, dried over sodium sulphate and filtered and the filtrate is concentrated under reduced pressure.

1.4 g of base are obtained, the hydrochloride of which is prepared by addition of 30 ml of diethyl ether saturated with gaseous hydrogen chloride.

After recrystallization, 0.65 g of white solid is obtained.
Melting point: 95–112° C.

EXAMPLE 7B (COMPOUND NO. 22B)

8-Benzoyl-N-[(3,4-dihydro-2H-1-benzopyran-2-yl)
methyl]-8-azabicyclo[3.2.1]octane-3-methanamine
hydrochloride A suspension of 0.6 g (1.9 mmol) of (3,4-dihydro-2H-1-benzopyran-2-yl)methyl 4-methylbenzenesulphonate, 1 g (4.1 mmol) of 8-benzoyl-8-azabicyclo[3.2.1]octane-3-methanamine and 0.26 g (1.9 mmol) of potassium carbonate in 11 ml of acetonitrile is prepared and is refluxed for 18 h.

A small amount of potassium iodide and an additional 0.15 g of potassium carbonate are added and the mixture is refluxed for a further 8 h.

The insoluble material is removed by filtration, the filtrate is concentrated under reduced pressure, the residue is taken up in dichloromethane, the solution is washed with water, dried over sodium sulphate and filtered, the filtrate is concentrated under reduced pressure and the residue is purified by chromatography on a column of silica gel, eluting with an 80/20 and then 70/30 mixture of ethyl acetate and methanol.

The hydrochloride is prepared using a 0.1 N solution of hydrochloric acid in 2-propanol.

0.4 g of solid is obtained.
Melting point: 148.5–151.5° C.

EXAMPLE 8B (COMPOUND NO. 24B)

8-Benzoyl-N-((4-oxo-2,3-dihydro-4H-1-benzopyran-
3-yl)methyl]-8-azabicyclo[3.2.1]octane-3-
methanamine hydrochloride 1.71 g (6.1 mmol) of 8-benzoyl-8-azabicyclo[3.2.1]octane-3-methanamine hydrochloride, 0.2 g (6.3 mmol) of paraformaldehyde and a few drops of concentrated hydrochloric acid in 10 ml of 2-propanol are introduced into a three-necked round-bottomed flask, the mixture is refluxed for 5 min, 0.78 g (5.3 mmol) of 2,3-dihydro-4H-1-benzopyran-4-one dissolved in 10 ml of 2-propanol is added and refluxing is continued for 18 h.

The mixture is cooled and the hydrochloride is collected directly by filtration.

1.26 g of solid are obtained.
Melting point: 187–189° C.

EXAMPLE 9B (COMPOUND NO. 29B)

(S)-exo-8-Benzoyl-N-[8-methoxy-2,3-dihydro-1,4-
benzodioxan-2-yl)methyl]-8-azabicyclo[3.2.1]
octane-3-methanamine hydrochloride (1:1)

9B.1. (S)-8-methoxy-1,4-benzodioxane-2-methanol
The preparation of this compound is described in *Tet. Letters* (1992) 33 6283–6286.

9B.2. (8-Methoxy-2,3-dihydro-1,4-benzodioxan-2-yl)
methyl (R)-4-methylbenzenesulphonate 410 mg (2.1 mmol) of (S)-8-methoxy-1,4-benzodioxane-2-methanol are dissolved in 5 ml of pyridine, 398 mg (2.1 mmol) of 4-methylbenzenesulphonyl chloride are added and the mixture is stirred at room temperature for 20 h. The mixture is poured onto 30 ml of ice-cold water and extracted with twice 15 ml of ethyl acetate, the organic phase is washed with aqueous 1 N hydrochloric acid solution, then with aqueous sodium hydrogen carbonate solution and then with water and is dried over sodium sulphate. This solution is filtered, the solvent is evaporated off under reduced pressure, the residue is taken up in pentane and the gummy solid is collected, washed with pentane and dried under reduced pressure.

405 mg of compound are isolated, which product is used without further purification in the following step.

9B.3. (S)-exo-8-Benzoyl-N-[8-methoxy-2,3-dihydro-1,4-
benzodioxan-2-yl)methyl]-8-azabicyclo[3.2.1]octane-3-
methanamine hydrochloride (1:1)

A suspension of 380 mg (1.08 mmol) of (8-methoxy-2,3-dihydro-1,4-benzodioxan-2-yl)methyl (R)-4-methylbenzenesulphonate, 530 mg (2.16 mmol) of 8-benzoyl-8-azabicyclo[3.2.1]octane-3-methanamine and 180 mg (1.3 mmol) of potassium carbonate in 50 ml of acetonitrile is prepared under an inert atmosphere and the mixture is refluxed for 57 h.

The solvent is evaporated off under reduced pressure, the residue is taken up in dichloromethane and water, the organic phase is separated out, washed with water to neutral pH and filtered, the solvent is evaporated off under reduced pressure and the residue is purified by chromatography on a column of silica gel, eluting with a 98/2 and then 95/5 mixture of dichloromethane and methanol.

The hydrochloride is prepared using a 0.1 N solution of hydrochloric acid in 2-propanol.

135 mg of solid are finally isolated.
Melting point: 210–211° C. $[\alpha]_D^{20}$=−53° (c=0.1, MeOH).

EXAMPLE 10B (COMPOUND NO. 31B)

(S)-exo-8-Benzoyl-N-[7-chloro-2,3-dihydro-1,4-benzodioxan-2-yl)methyl]-8-azabicyclo[3.2.1]octane-3-methanamine hydrochloride (1:1)

10B.1. (7-Chloro-2,3-dihydro-1,4-benzodioxan-2-yl)methyl (R)-4-methylbenzenesulphonate The preparation of this compound is described in patent application WO 97/03071, pages 42–43.

10B.2. (S)-exo-8-Benzoyl-N-[7-chloro-2,3-dihydro-1,4-benzodioxan-2-yl)methyl]-8-azabicyclo[3.2.1]octane-3-methanamine hydrochloride (1:1)

A suspension of 1.1 g (3.1 mmol) of (7-chloro-2,3-dihydro-1,4-benzodioxan-2-yl)methyl (R)-4-methylbenzenesulphonate, 1.5 g (6.2 mmol) of 8-benzoyl-8-azabicyclo[3.2.1]octane-3-methanamine and 515 mg (3.7 mmol) of potassium carbonate in 20 ml of acetonitrile is prepared and is refluxed for 48 h.

The solvent is evaporated off under reduced pressure, the residue is taken up in dichloromethane and water, the organic phase is separated out, washed to neutral pH, dried over sodium sulphate and filtered, the filtrate is evaporated under reduced pressure and the residue is purified by chromatography on a column of silica gel, eluting with a 98/2 and then 95/5 mixture of dichloromethane and ethanol.

The hydrochloride is prepared using a 0.1 N solution of hydrochloric acid in 2-propanol.

230 mg of solid are finally isolated.

Melting point: 164.5–167° C. $[\alpha]_D^{20} = -56°$ (c=0.1, MeOH).

Tables A and B below illustrate the chemical structures and physical properties of a number of compounds of the invention.

TABLE A (IA)

| No. | V | Y | Z | Isom | Salt | m.p, (° C.) |
|---|---|---|---|---|---|---|
| 1A | H | H | O | β | HCl 1:1 | 206–208.5 |
| 2A | H | 3-OCH$_2$CH$_3$ | O | β | HCl 1:1 | 144–146.5 |
| 3A | H | 3-Cl | O | β | HCl 1:1 | 213–215 |
| 4A | H | H | H,H | β | fum 5:2 | 190–192 |
| 5A | H | 4-Cl | H,H | β | fum 2:1 | 198–199 |
| 6A | H | 3-Cl | H,H | β | fum 2:1 | 210–211 |
| 7A | 4,7-(OCH$_3$)$_2$ | H | O | β | HCl 1:1 | 138–141 |
| 8A | 4,7-(OCH$_3$)$_2$ | 3-Cl | O | β | HCl 1:1 | 222.5–225 |
| 9A | 4,7-(OCH$_3$)$_2$ | 3-OCH$_3$ | O | β | HCl 1:1 | 213–214.5 |
| 10A | 4,7-(OCH$_3$)$_2$ | 4-Cl | O | β | HCl 1:1 | 226–228 |
| 11A | 4,7-(OCH$_3$)$_2$ | 3,4-Cl$_2$ | O | β | HCl 1:1 | 215–217 |
| 12A | 4,7-(OCH$_3$)$_2$ | 3,4-(OCH$_3$)$_2$ | O | β | HCl 1:1 | 134–136 |
| 13A | 4,7-(OCH$_3$)$_2$ | 3-OCH$_2$CH$_3$ | O | β | HCl 1:1 | 161–163 |
| 14A | 4,7-(OCH$_3$)$_2$ | H | H,H | β | fum 2:1 | 187–189 |

The geometrical isoform of the azabicyclooctane ring-system is indicated in the "Isom" column.

In the "Salt" column, "HCl" denotes a hydrochloride and "fum" denotes an (E)-2-butenedioate, or fumarate; the acid:base molar ratios are indicated.

(IB)

| No. | X | W | n | Z | V | Y | R | Isom | Salt | m.p. (° C.) |
|---|---|---|---|---|---|---|---|---|---|---|
| 1B | O | O | 1 | H,H | H | H | H | β | fum 2:1 | 105–107 |
| 2B | O | O | 1 | H,H | H | 3-OCH$_3$ | H | β | fum 2:1 | 77–85 |
| 3B | O | O | 1 | H,H | H | 3-OCH$_2$CH$_3$ | H | β | fum 1:1 | 126–129 |
| 4B | O | O | 1 | H,H | H | 3-F | H | β | fum 1:1 | 132–134 |
| 5B | O | O | 1 | H,H | H | 3-Cl | H | β | fum 2:1 | 111–116 |
| 6B | O | O | 1 | H,H | H | 3-CH$_3$ | H | β | fum 2:1 | 142–146 |
| 7B | O | O | 1 | H,H | H | 4-Cl | H | β | fum 2:1 | 206–207 |
| 8B | O | O | 1 | H,H | H | H | (CH$_2$)$_2$CH$_3$ | β | fum 2:1 | 190–191 |
| 9B | O | O | 1 | O | H | H | H | β | HCl 1:1 | 80–90 |
| 10B | O | O | 1 | O | H | 3-OCH$_3$ | H | β | HCl 1:1 | 181–183 |
| 11B | O | 0 | 1 | O | H | 3-OCH$_2$CH$_3$ | H | β | HCl 1:1 | 192–194 |
| 12B | O | O | 1 | O | H | 3-F | H | β | HCl 1:1 | 206–209 |
| 13B | O | O | 1 | O | H | 3-Cl | H | β | HCl 1:1 | 91–100 |
| 14B | O | O | 1 | O | H | 3-CH$_3$ | H | β | HCl 1:1 | 213–214 |
| 15B | O | O | 1 | O | H | 4-OCH$_3$ | H | β | HCl 1:1 | 93–110 |
| 16B | O | O | 1 | O | H | 4-Cl | H | β | — | 123–124 |
| 17B | O | O | 1 | O | H | 4-CH$_3$ | H | β | HCl 1:1 | 217.5–219 |
| 18B | O | O | 1 | O | 7-Cl | H | H | β | HCl 1:1 | 217.5–219 |

-continued

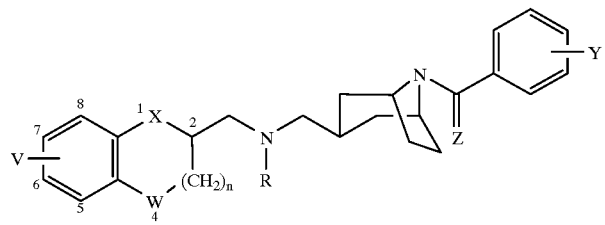
(IB)

| No. | X | W | n | Z | V | Y | R | Isom | Salt | m.p. (° C.) |
|---|---|---|---|---|---|---|---|---|---|---|
| 19B | O | O | 1 | O | 5-F | H | H | β | HCl 1:1 | 104–109 |
| 20B | O | O | 1 | O | H | H | (CH$_2$)$_2$CH$_3$ | β | HCl 1:1 | 80–115 |
| 21B | O | O | 1 | O | H | 4-CH$_3$ | (CH$_2$)$_2$CH$_3$ | β | HCl 1:1 | 95–112 |
| 22B | O | CH$_2$ | 1 | O | H | H | H | β | HCl 1:1 | 148.5–151.5 |
| 23B | CH$_2$ | O | 1 | O | H | H | H | β | HCl 1:1 | 84–104 |
| 24B | CO | O | 1 | O | H | H | H | β | HCl 1:1 | 187–189 (d) |
| 25B | CO | O | 1 | O | 7-CH$_3$ | H | H | β | HCl 1:1 | 181–183.5 |
| 26B | CO | O | 1 | O | 5-CH$_3$ | H | H | β | HCl 1:1 | 189–191 |
| 27B | O | O | 1 | O | 5-OCH$_3$ | H | H | β | HCl 1:1 | 122–123 |
| 28B | O | O | 1 | O | 8-OCH$_3$ | H | H | β | HCl 1:1 | 218.5–220 |
| 29B | O | O | 1 | O | 3-OCH$_3$ | H | H | (S)-β | HCl 1:1 | 210–211 $[\alpha]_D^{20} = -53°$ |
| 30B | O | O | 1 | O | 8-OCH$_3$ | H | H | (R)-β | HCl 1:1 | 211–213 $[\alpha]_D^{20} = +52°$ |
| 31B | O | O | 1 | O | 7-Cl | H | H | (S)-β | HCl 1:1 | 164.5–167 $[\alpha]_D^{20} = -56°$ |
| 32B | O | O | 1 | O | 7-Cl | H | H | (R)-β | HCl 1:1 | 181–183 $[\alpha]_D^{20} = +51$ |
| 33B | O | O | 1 | O | 8-OCH$_3$ | 4-CH$_3$ | H | β | HCl 1:1 | 175–176 |
| 34B | O | O | 1 | O | 8-OCH$_3$ | 3-OCH$_2$CH$_3$ | H | β | HCl 1:1 | 102–103 |
| 35B | O | O | 1 | O | 7-Cl | 3-CH$_3$ | H | β | HCl 1:1 | 128–130 |
| 36B | O | O | 1 | O | 7-Cl | 3-OCH$_3$ | H | β | HCl 1:1 | 190–193.5 |
| 37B | O | O | 1 | O | 6-F | H | H | β | HCl 1:1 | 115 |

The numbering of the atoms in the heterocycle containing W and X is given as a guide, essentially to locate the substituent V; it does not necessarily conform to the nomenclature rules, in particular when X represents a CH$_2$ or CO group.

The geometrical isoform of the azabicyclooctane ring-system is indicated in the "Isom" column. The terms (R) and (S) relate to the atom in the 2-position of the 2,3-dihydro-1,4-dioxane ring.

In the "Salt" column, "—" denotes a compound in base form, "HCl" denotes a hydrochloride and "fum" denotes an (E)-2-butenedioate, or fumarate; the acid:base molar ratios are indicated.

In the "m.p. (° C.)" column, "(d)" indicates a melting point with decomposition. The optical rotations of compounds 29 to 32 are given for (c=0.1, MeOH).

The compounds of the invention underwent a series of pharmacological tests which revealed their value as therapeutically active substances.

Study of the Affinity for D$_2$-type Dopaminergic Receptors in Rat Striatum

The compounds displace the binding of a specific labelled ligand, spiperone (referred to hereinbelow as "[$^3$H] spiperone" and described by Briley and Langer., Eur. J. Pharmacol. (1978), 50, 283), on the D$_2$ receptors present in rat striatum.

The animals used are 150 to 250 g male Sprague-Dawley rats. After decapitation, the brain is removed and the striatum is excised. The tissue is ground using a Polytron™ grinder in 50 volumes of 50 mM Tris-HCl buffer containing sodium chloride (120 mM), potassium chloride (5 mM) and the pH of which is adjusted to 7.4 (i.e. 100 mg of fresh tissue per 5 ml). The homogenized tissues are washed twice at 4° C., centrifuging them each time for 10 min at 40,000×g and resuspending the pellet in fresh cooled buffer. Lastly, the final pellet is suspended in the same volume of buffer and ascorbic acid (0.1% final concentration) and pargyline (10 μM final concentration) are added. The mixture is then incubated at 37° C. for 10 min.

The binding of [$^3$H]spiperone (New England Nuclear, specific activity 20–40 mCi/mmol) is determined by incubating 100 μl of the membrane suspension with the radioligand (0.25 nM) in a final volume of 1 ml, for 20 minutes at 37° C., in the presence or absence of the test compound. The non-specific binding is determined in the presence of haloperidol at the concentration of 10 μM. After incubation, the membranes are recovered by filtration on Whatman GF/B™ filters, which are washed with two volumes of 5 ml of ice-cold buffer. The filters are extracted in the scintillation liquid and the radioactivity is measured by liquid scintigraphy with an efficacy of 50 to 60%. For each test compound, the results are expressed by the IC$_{50}$, that is to say by the concentration which inhibits the binding of [$^3$H]spiperone by 50%, calculated by a graphical or mathematical method.

For the compounds of the invention, the IC$_{50}$ values are between 0.05 and 2 μM.

Study of the Affinity for the D$_3$ Dopaminergic Receptors in Bovine Novau Caude The compounds underwent an in vitro study regarding their affinity for the D$_3$ dopaminergic receptors obtained from a membrane preparation of bovine noyau caudé, essentially as described by Schoemaker H. in Eur. J. Pharmacol. (1993), 242, R1–R2.

On the day of the experiment, the bovine noyaux caudés (Collect Organe, Paris, France), stored at −80° C., are thawed and homogenized at 40° C. in 10 volumes of buffer (10 mM Tris, 1 mM EDTA, pH 7.5 at 25° C.) using a Polytron™ (position 5, 30 s). The homogenate is centrifuged at 2500 g for 1 min (Sorvall™ centrifuge fitted with an SS34 rotor). The supernatant is recovered and centrifuged at 35,000 g for 15 min, the pellet is washed by resuspension in 10 volumes of buffer, homogenization and centrifugation, and the final pellet is suspended in 10 volumes of buffer and preincubated at 37° C. for 10 min.

The homogenate is centrifuged at 35,000 g for 15 min and the pellet is resuspended in the incubation buffer (50 mM HEPES, 1 mM EDTA, 50 $\mu$M 8-hydroxy-quinoline, 0.005% ascorbic acid, pH 7.5 at 25° C.) in a proportion of 100 mh of initial tissue per ml.

The membrane suspension (150 $\mu$l) is incubated at 23° C. for 60 min in tubes, in the presence of 0.8 nM [$^3$H]7-OH-DPAT (specific activity 120–160 Ci/mmol, Amersham™) in a final volume of 1 ml of incubation buffer containing 0.2 $\mu$M zolpidem hydrochloride and 1 mg of bovine serum albumin, in the presence or absence of test compound. The incubation is stopped by filtration on a Brandel Harvester M-48™, using Whatman GF/C™ filters pretreated with bovine serum albumin (0.1%) for 30 min. After predilution with 4 ml of buffer (50 mM Tris, 120 mM NaCl, 5 mM KCl, pH 7.4 at 25° C.) of each reaction medium, the tubes are rinsed twice with 4 ml of this buffer.

The filters are cut up and then dried in an oven at 120° C. for 10 min and the radioactivity retained on the filters is determined by liquid scintillation spectrometry. The non-specific binding is determined in the presence of 1 $\mu$M of dopamine.

For each concentration of test compound, the percentage of inhibition of specific binding of the [$^3$H]7-OH-DPAT is calculated, after which the IC$_{50}$, the concentration which inhibits the binding by 50% is determined.

The IC$_{50}$ values of the compounds of the invention are of the order of 0.01 $\mu$M to 2 $\mu$M.

Study of the Affinity for 5-HT$_{1A}$-type Serotoninergic Receptors

The compounds displace the binding of a specific labelled ligand, [$^3$H]-8-hydroxy-2-di-n-propylamino tetraline (referred to hereinbelow as "[$^3$H]-8-OH-DPAT" and described by Gozlan et al., Nature (1983), 305, 140), on the 5-HT$_{1A}$ receptors present in rat hippocampus.

The animals used are 160 to 200 g male Sprague-Dawley rats. After decapitation, the brain is removed and the hippocampus is excised. The tissue is ground in an Ultra-Turrax Polytron™ machine for 30 s at the half-maximal speed in 10 volumes of 50 mM Tris buffer of pH adjusted to 7.4 with hydrochloric acid (i.e. 100 mg of fresh tissue per ml). The homogenized tissues are washed twice at 4° C., centrifuging them each time for 10 min at 48,000×g and resuspending the pellet in fresh cooled buffer. Lastly, the final pellet is suspended in the buffer to give a concentration of 50 mg of starting tissue per ml of buffer at 50 mM. The mixture is then incubated at 37° C. for 10 min.

The binding with [$^3$H]8-OH-DPAT (1 nM) is determined by incubation of 50 $\mu$l of membrane suspension in a final volume of 250 $\mu$l of buffer containing 10 $\mu$M of pargyline and 3 $\mu$M of paroxetine. After incubation for 15 min at 37° C., the membranes are recovered by filtration on Whatman GF/B™ filters, which are washed three times with 5 ml aliquots of ice-cold buffer. The filters are extracted in the scintillation liquid and the radioactivity is measured by liquid scintigraphy. The specific binding of the [$^3$H]8-OH-DPAT is defined as the amount of radioactivity retained on the filters and which may be inhibited by co-incubation with 10 $\mu$M 5-hydroxytryptamine. At a concentration of 1 nM of [$^3$H]8-OH-DPAT, the specific binding represents 90% of the total radioactivity collected on the filter.

For each concentration of test compound, the percentage of inhibition of the binding with [$^3$H]8-OH-DPAT is determined, and then the IC$_{50}$ concentration, the concentration which inhibits the binding by 50%.

For the compounds of the invention, the IC$_{50}$ values are between 0.1 and 500 nM.

Study of the Affinity for the 5-HT$_2$-type Serotoninergic Receptors

The compounds of the invention also underwent an in vitro study of displacement of the binding of spiperone on the serotoninergic (5-HT$_2$) receptors of rat cerebral cortex.

For this test, the rat brains are removed, the cortex is dissected therefrom and is homogenized at 0° C. in 10 volumes of a mixture containing, per litre, 50 millimol of Tris/HCl buffer at pH=7.4, 120 millimol of sodium chloride and 5 millimol of potassium chloride. The homogeneous mixture is centrifuged at 40,000×g for 10 min, after which the pellet is recovered and is washed by suspending it in the same buffer mixture, it is homogenized again and is centrifuged, this treatment of the pellet being carried out twice. Lastly, the final pellet is diluted in the same buffer mixture, in a proportion of 100 mg of wet tissue per 1 ml of buffer.

The tissue is then preincubated for 10 min at 37° C. in the presence of 10 micromol/l of pargyline, followed by incubation for 20 min at 37° C. in the presence of [$^3$H]spiperone (specific activity: 15 to 30 Ci per millimole) at a concentration of 0.3 nanomol/l and of the test compound.

The membranes are then collected by filtration on Whatman GF/B™ filters which are washed twice with 5 ml of cold buffer. The radioactivity retained on the filter is measured by liquid scintigraphy.

In order to evaluate the activity of the compounds, the curve of the percentage inhibition of the specific binding of [$^3$H]spiperone is established as a function of the concentration of displacing drug. The IC$_{50}$, concentration, the concentration which inhibits the specific binding by 50%, is determined graphically.

The specific binding is defined as being the binding displaced by 100 micromol/l of 5-HT.

The IC$_{50}$ concentrations of the compounds of the invention are between 0.02 and 5 $\mu$M.

The results of the tests show that the compounds of the invention have strong affinity for D$_2$-type and D$_3$-type dopaminergic receptors and for 5-HT$_{1A}$-type and 5-HT$_2$-type serotoninergic receptrs. These results suggest that the compounds can be used for the treatment of complaints and pathologies associated with dopaminergic and serotoninergic transmission dysfunction, in particular of the D$_2$ and D$_3$ dopaminergic receptors and 5-HT$_{1A}$ and 5-HT$_2$ serotoninergic receptors.

Thus, they can be used for the treatment of psychoses, in particular schizophrenia (deficient form and productive form) and acute or chronic extrapyramidal symptoms induced by neuroleptic agents, for the treatment of various forms of anxiety, panic attacks, phobias, compulsive obsessional disorders, for the treatment of various forms of depression, including psychotic depression, for the treatment of disorders due to alcohol abuse or withdrawal, sexual behaviour disorders, eating disorders and for the treatment of migraine.

To this end, they may be in any form appropriate for administering them orally or parenterally, combined with any suitable excipient, and may be dosed to allow a daily dosage of from 1 to 1000 mg.

What is claimed is:

1. A compound in the form of a pure geometrical isomer or a mixture of such isomers, corresponding to the general formula (I)

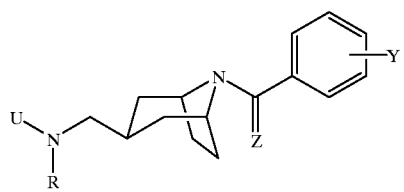

(I)

in which

U represents

A) either a 2,3-dihydro-1H-inden-2-yl group of general formula (A)

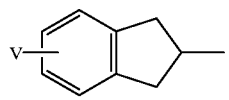

(A)

B) or a heterocyclic group of general formula (B)

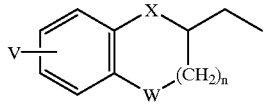

(B)

in which

V represents a hydrogen or halogen atom, a ($C_1$–$C_3$) alkyl group or one or two ($C_1$–$C_3$) alkoxy groups, W and X each represent, respectively, either two oxygen atoms, or an oxygen atom and a $CH_2$ group, or a $CH_2$ group and an oxygen atom, or an oxygen atom and a CO group, n represents the number 0 or 1, R represents either a propyl group when U represents a 2,3-dihydro-1H-inden-2-yl group of general formula (A), or a hydrogen atom or a ($C_1$–$C_3$) alkyl group when U represents a heterocyclic group of general formula (B), Y represents one or more atoms or groups chosen from the following: hydrogen, halogen, ($C_1$–$C_3$) alkyl and ($C_1$–$C_3$) alkoxy, and Z represents two hydrogen atoms or an oxygen atom;

or a pharmaceutically acceptable acid-addition salt thereof.

2. A compound according to claim 1, wherein it corresponds to the general formula (IA)

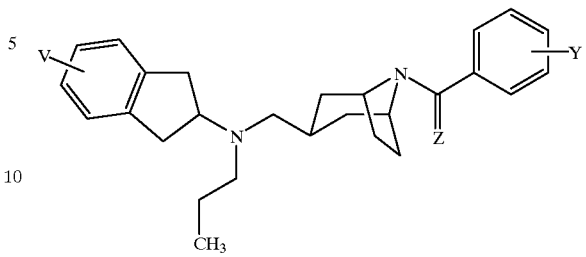

(IA)

in which V, Y and Z are as defined in claim 1.

3. A compound according to claim 1, wherein it corresponds to the general formula (IB)

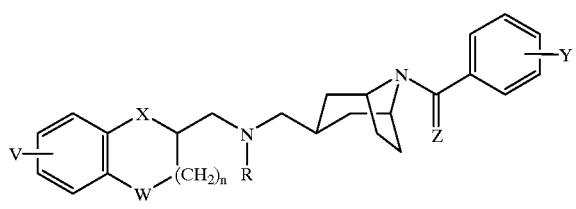

(IB)

in which V, W, X, Y and Z are as defined in claim 1.

4. A pharmaceutical composition, comprising a compound according to claim 1, combined with an excipient.

5. (S)-exo-8-Benzoyl-N-[7-chloro-2,3-dihydro-1,4-benzodioxan-2-yl)methyl]-8-azabicyclo[3.2.1]octane-3-methananine, or a pharmaceutically acceptable acid addition salt thereof according to claim 3.

6. (S)-exo-8-Benzoyl-N-[7-chloro-2,3-dihydro-1,4-benzodioxan-2-yl)methyl]-8-azabicyclo[3.2.1]octane-3-methananine hydrochloride according to claim 5.

7. A pharmaceutical composition comprising a compound according to claim 2 combined with an excipient.

8. A pharmaceutical composition comprising a compound according to claim 3 combined with an excipient.

9. A pharmaceutical composition comprising a compound according to claim 5 combined with an excipient.

10. A pharmaceutical composition comprising a compound according to claim 6 combined with an excipient.

11. A method for the treatment of complaints and pathologies associated with dopaminergic and/or serotoninergic transmission dysfunction in a patient in need of such treatment which comprises administering an effective amount of a compound according to claim 1.

12. A method for the treatment of complaints and pathologies associated with dopaminergic and/or serotoninergic transmission dysfunction in a patient in need of such treatment which comprises administering an effective amount of a compound according to claim 2.

13. A method for the treatment of complaints and pathologies associated with dopaminergic and/or serotoninergic transmission dysfunction in a patient in need of such treatment which comprises administering an effective amount of a compound according to claim 3.

14. A method for the treatment of complaints and pathologies associated with dopaminergic and/or serotoninergic transmission dysfunction in a patient in need of such treatment which comprises administering an effective amount of a compound according to claim 5.

15. A method for the treatment of complaints and pathologies associated with dopaminergic and/or serotoninergic transmission dysfunction in a patient in need of such treatment which comprises administering an effective amount of a compound according to claim 6.

16. A method according to claim 11 for the treatment of psychoses or anxiety.

17. A method according to claim 14 for the treatment of psychoses or anxiety.

18. A method according to claim 15 for the treatment of psychoses or anxiety.

19. A method according to claim 17 where as said psychoses is schizophrenia.

20. A method according to claim 18 where as said psychoses is schizophrenia.

* * * * *